(12) United States Patent
Gatineau et al.

(10) Patent No.: US 10,309,010 B2
(45) Date of Patent: Jun. 4, 2019

(54) COBALT-CONTAINING COMPOUNDS, THEIR SYNTHESIS, AND USE IN COBALT-CONTAINING FILM DEPOSITION

(71) Applicants: L'Air Liquide, Société Anonyme pour l'Etude et l'Exploitation des Procédés Georges Claude, Paris (FR); Satoko Gatineau, Seoul (KR); Changhee Ko, Tsukuba (JP); Jean-Marc Girard, Versaillles (FR); Julien Gatineau, Seoul (KR)

(72) Inventors: Satoko Gatineau, Seoul (KR); Changhee Ko, Tsukuba (JP); Jean-Marc Girard, Versaillles (FR); Julien Gatineau, Seoul (KR)

(73) Assignee: L'Air Liquide, Société Anonyme pour l'Etude et l'Exploitation des Procédés Georges Claude, Paris (FR)

( * ) Notice: Subject to any disclaimer, the term of this patent is extended or adjusted under 35 U.S.C. 154(b) by 803 days.

(21) Appl. No.: 14/765,090

(22) PCT Filed: Jan. 31, 2014

(86) PCT No.: PCT/IB2014/058712
§ 371 (c)(1),
(2) Date: Jul. 31, 2015

(87) PCT Pub. No.: WO2014/118748
PCT Pub. Date: Aug. 7, 2014

(65) Prior Publication Data
US 2016/0010204 A1    Jan. 14, 2016

Related U.S. Application Data (60) Provisional application No. 61/759,134, filed on Jan. 31, 2013.

(51) Int. Cl.
*C23C 16/06* (2006.01)
*C07F 15/06* (2006.01)
(Continued)

(52) U.S. Cl.
CPC .............. *C23C 16/06* (2013.01); *C07F 15/06* (2013.01); *C23C 16/18* (2013.01); *C23C 16/28* (2013.01);
(Continued)

(58) Field of Classification Search
CPC ... C23C 16/06; C23C 16/45525; C23C 16/28; C23C 16/40; C23C 16/45553;
(Continued)

(56) References Cited

U.S. PATENT DOCUMENTS 4,814,294 A * 3/1989 West ...................... C23C 16/42
257/E21.13
6,346,477 B1    2/2002 Kaloyeros et al.
(Continued)

FOREIGN PATENT DOCUMENTS

JP        2010 84215        4/2015

OTHER PUBLICATIONS

Aylett et al., "Chemical Vapour Deposition of Transition-Metal Silicides by Pyrolysis of Silyl Transition-Metal Carbonyl Compounds", J.C.S.( Dalton 1977) pp. 2058-2061.*
(Continued)

*Primary Examiner* — Michael P Wieczorek
*Assistant Examiner* — Michael G Miller
(74) *Attorney, Agent, or Firm* — Patricia E. McQueeney; Allen E. White (57) ABSTRACT

Cobalt-containing compounds, their synthesis, and their use for the deposition of cobalt containing films are disclosed. The disclosed cobalt-containing compounds have one of the following formulae: wherein each of $R^1$, $R^2$, $R^3$, $R^4$ and $R^5$ is independently selected from the group consisting of hydrogen and linear, cyclic, or branched hydrocarbon groups; provided that (a) $R^1 \neq R^2$ and/or $R^3$ when $R^1$ and $R^2$ and $R^3$ are a hydrocarbon group; (b) $R^1$ and $R^2$ are a hydrocarbon group when $R^3$ is H; or (c) $R^1$ is a C2-C4 hydrocarbon group when $R^2$ and $R^3$ are H.

18 Claims, 4 Drawing Sheets

(51) Int. Cl.
| | |
|---|---|
| C23C 16/18 | (2006.01) |
| C23C 16/34 | (2006.01) |
| C23C 16/40 | (2006.01) |
| C23C 16/42 | (2006.01) |
| C23C 16/455 | (2006.01) |
| C23C 16/28 | (2006.01) |
| H01L 21/285 | (2006.01) |
| H01L 21/768 | (2006.01) |

(52) U.S. Cl.
CPC .............. *C23C 16/34* (2013.01); *C23C 16/40* (2013.01); *C23C 16/406* (2013.01); *C23C 16/42* (2013.01); *C23C 16/45525* (2013.01); *C23C 16/45553* (2013.01); *H01L 21/28518* (2013.01); *H01L 21/28556* (2013.01); *H01L 21/76841* (2013.01)

(58) Field of Classification Search
CPC ....... C23C 16/42; C23C 16/406; C23C 16/34; C23C 16/18; C07F 15/06; H01L 21/76841; H01L 21/28856; H01L 21/28518
USPC ............................. 427/248.1–255.7, 569–579
See application file for complete search history.

(56) References Cited

U.S. PATENT DOCUMENTS

| | | | |
|---|---|---|---|
| 6,984,591 B1 * | 1/2006 | Buchanan | C23C 16/16 257/751 |
| 2007/0202254 A1 * | 8/2007 | Ganguli | C23C 16/18 427/252 |

OTHER PUBLICATIONS

Begum et al, "Synthesis, Reaction and Thermal Decomposition of a Silicon-Cobalt Bonded Compound", Journal of Bangladesh Academy of Sciences, vol. 17, No. 2( 1993) pp. 201-205.*
MacDiarmid, A.G. et al., "Properties of silicon derivates of cobalt, manganese, and iron carbonyls," Pure and Applied Chemistry (1969) vol. 19, Issue 3, 431-438 (Year: 1969).*
Abraham, K.M. et al., "Synthesis of heteropolymetallic silanes," Inorganic Chemistry, 1973, vol. 12, No. 1, 2850-2856.
Almond, M.J., "Short-lived molecules," Angew, Chem. 103 (1991) No. 8, 1063.
Air Liquide, "New cobalt precursors and their process evaluation by CVD," poster, Atomic Layer Deposition Conference, Jun. 28-30, 2015, Portland, Oregon, ALD2015 Poster Session I, 350.
Aylett, B.J. et al., "Chemical vapor deposition of metal silicides from organometallic compounds with silicon-metal bonds," Vacuum, 1985, vol. 35, Nos. 10-11, 435-439.
Baay, Y.L. et al, "Synthesis and properties of trimethylsilyl cobalt tetracarbonyl and related compounds," Inorg. Nucl. Chem. Letters, 1967, vol. 3, 159-161.
Baay, Y.L. et al., "Trimethyl- and trichlorosilylcobalt tetracarbonyls and the hydrosilation of ethylene," Inorganic Chemistry, vol. 8, No. 4, Apr. 1969, 986-994.
Begum, R et al., "Synthesis, reaction and thermal decomposition of a silicon-cobalt bonded compound," Journal of Bangladesh Academy of Sciences, 1993, vol. 17, No. 2, 201-205.
Bradley, G.F. et al., "Reaction of octacarbonyldicobalt with organosilanes, -germanes, and -stannanes: Formation, properties, and vibrational spectra of trimethylgermyltetracarbonylcobalt and related complexes," Journal of the Chemical Society, Dalton Transactions: Inorganic Chemistry, 1974, vol. 3, 264-269.
Braunstein, P. et al., "New mono- and polynuclear iron silylene and stannylene complexes," Organometallics, 2001, vol. 20, No. 4, 627-633.

Cerveau, G. et al., "Cleavage of silicon- and germanium-transition metal bonds. Dependence of the stereochemistry on the nature of the ligands and the geometry of complexes," Journal of Organometallic Chemistry, 1982, vol. 236, No. 1, 33-52.
Chatani, N. et al., Cobalt carbonyl catalyzed reactions of esters and lactones with hydrosilane and carbon monoxide. A novel synthetic method for the introduction of the siloxymethylidene group, J. Am. Chem. Soc., 1986, vol. 108, 7361-7373.
Chatani, N. et al., "A new entry to pi-allylcobalt tricarbonyls using $(CH_3)_3SiCo(CO)_4$," Tetrahedron Letters, 1983, vol. 24, No. 50, 5649-5652.
Cutler, A.R., "Selective transformation of carbonyl ligands to organic molecules," Progress Report for Period Sep. 1, 2011-Nov. 14, 1992, prepared for the U.S. Department of Energy on May 12, 1992, 23 pages.
Emeleus, H.J., "B. Transition metal derivatives," Advances in Inorganic Chemistry and Radiochemistry, 1982, 6 pages.
Gleizes, A.N., "MOCVD of chalcogenides, pnictides, and heterometallic compounds from single-source molecule precursors," Chemical Vapor Deposition, 2000, vol. 6, No. 4, 155-173.
Gusbeth, P. et al., "µ3-Silidyne heterometal clusters," Chemische Berichte, 1985, vol. 118, No. 3, 1143-1153.
Ingle, W.M. et al., "Cobalt to oxygen migration of the trimethylsilyl group in trimethylsilylcobalt tetracarbonyl," Journal of the Chemical Society, 1973, vol. 14, 497-498.
Kreisz, J. et al., "Reaction of silylcobalt tetracarbonyls with oxiranes. Kinetics and mechanism," Journal of Organometallic Chemistry, 1993, vol. 451, Nos. 1-2, 53-57.
Morrison, D.L. et al., "13. Tricholor-, trimethyl-, and trifluorosilylcobalt tetracarbonyl," Inorganic Synthesis, 1971, vol. 13, 65-73.
Prokop, J. et al., "nm-$Co_2Si$, CoSi and $CoSi_2$ silicide films from the single source precursor $CoSiCl_3(CO)_4$ in the presences of $SiH_4$," Thin Solid Films, 2000, vol. 359, 39-45.
Reichel, C.L. et al., "Photochemistry of cobalt carbonyl complexes having a cobalt-silicon bond and its importance in activation of catalysis," Inorg. Chem., 1980, vol. 19, 3858-3860.
Safiullah, S. et al., "Synthesis and characterization of complexes $Me_2Si[Co(CO)_3]_2$ (dppe)," Journal of the Bangladesh Chemical Society, 1996, vol. 9, No. 1, 117-120.
Schmid, G. et al., "Silylene-metal complexes. 4. Base-stabilized silyleneiron complexes," Angewandte Chemie International Edition, 1977, vol. 16, No. 11, 785-786.
Sisak, A. et al., "Formation and multinuclear magnetic resonance investigation of silylammonium tetracarbonylcobaltate contact ion pairs," Central European Journal of Chemistry, 2006, 4(2), 299-316.
Sommer, L.H. et al., "Stereochemistry of asymmetric silicon. XV. Stereospecific hydrosilation and exchange reactions of $R_3Si*H(D)$ catalyzed by Group VIII metal centers," Journal of the American Chemical Society, 1969, vol. 91, No. 25, 7051-7061.
International Search Report and Written Opinion for corresponding PCT/IB2014/058712, dated Apr. 28, 2014.
International Search Report for related PCT/IB2014/058711, dated Apr. 28, 2014.
Gregg, B.T. et al., "Hydrosilation of the mangese acetyl (CO)5MnC(O)CH3 with monodydrosilanes," J. Am. Chem. Soc. 1996, 118, 10069-10084.
Kodas, T.T. et al., "The chemistry of metal CVD," ch. 9.2: classification of precursors, 431-435, Wiley-VCH publishers, Jan. 15, 1994.
Marczinowski, F., "Manganese in indium arsenide—charge switching and electronic structure on the atomic scale," Dissertation, University fo Hambur, Germany, 2010, 141 pages.
Schmitt, A.L. et al., "Synthesis and Applications of Metal Silicide Nanowires," J. Mater. Chem. 2010, 20, 223-235.
MacDiarmid, A.G. et al., "Properties of silicon derivates of cobalt, manganese, and iron carbonyls," Pure and Applied Chemistry (1969) vol. 19, Issue 3, 431-438.

* cited by examiner

COBALT-CONTAINING COMPOUNDS, THEIR SYNTHESIS, AND USE IN COBALT-CONTAINING FILM DEPOSITION

CROSS REFERENCE TO RELATED APPLICATIONS

This application is a 371 of International Application No. PCT/IB2014/058712 filed Jan. 31, 2014 which claims priority to U.S. provisional application No. 61/759,134 filed Jan. 31, 2013, the entire contents of each being incorporated herein by reference.

TECHNICAL FIELD

Cobalt-containing compounds, their synthesis, and their use for the deposition of cobalt-containing films are disclosed.

BACKGROUND

Chemical Vapor Deposition (CVD) and Atomic Layer Deposition (ALD) have been applied as main deposition techniques for producing thin films for semiconductor devices. These methods enable the achievement of conformal films (metal, oxide, nitride, silicide, etc.) through fine tuning of parameters during the deposition processes. Mainly the film growth is controlled by chemical reactions of metal-containing compounds (precursors) and the development of optimum precursors is essential under prediction of their properties and reaction processes.

Films of metal and metal silicide, particularly manganese, iron, cobalt, nickel, and ruthenium, are becoming important for a variety of electronics and electrochemical applications. For example, cobalt thin films are of interest due to their high magnetic permittivity. There are many reports of using cobalt thin films to form cobalt disilicide ($CoSi_2$) for Ohmic contacts owing to its low resistivity in front-end-of-the-line processing of semiconductor devices. Cobalt containing thin films were recently studied as Cu/low-k barriers, passivation layers, and capping layers for ultra-large scale integrated devices.

Synthesis methods of substituted silyl or halide cobalt tetracarbonyl complexes ($R_3SiCo(CO)_4$) are known (Sisak et al., Formation and Multinuclear Magnetic Resonance Investigation of Silylammonium Tetracarbonylcobaltate Contact Ion Pairs, Central European Journal of Chemistry, 4(2) (2006) pp. 299-316; Begum et al. Synthesis, Reaction and Thermal Decomposition of a Silicon-Cobalt Bonded Compound, Journal of Bangladesh Academy of Sciences, Vol. 17, No. 2 (1993) pp. 201-205; Chatani et al., Cobalt Carbonyl Catalyzed Reactions of Esters and Lactones with Hydrosilane and Carbon Monoxide. A Novel Synthetic Method for the Introduction of the Siloxymetahylidene Group, J. Am. Chem. Soc. (1986) 108, pp. 7361-7373; Chatani et al., A New Entry to π-Allylcobalt Tricarbonyls Using $(CH_3)_3SiCo(CO)_4$, Tetrahedron Letters, Vol. 24, No. 50 (1983) pp. 5649-5652; Reichel et al., Photochemistry of Cobalt Carbonyl Complexes Having a Cobalt-Silicon Bond and Its Importance in Activation of Catalyis, Inorg. Chem. 19 (1980) pp. 3858-3860; Bradley et al., Reaction of Octacarbonyldicobalt with Organosilanes, -germanes, and -stannanes. Formation, Properties, and Vibrational Spectra of (Trimethylgermyl)tetracarbonylcobalt and Related Complexes, Journal of the Chemical Society, Dalton Transactions: Inorganic Chemistry (1974) 3, pp. 264-9; Ingle et al., Cobalt to Oxygen Migration of the Trimethylsilyl Group in Trimethylsilylcobalt Tetracarbonyl, Journal of the Chemical Society, (1973) 14, pp. 497-498; Morrison et al., Trichloro-, Trimethyl-, and Trifluorosilylcobalt Tetracarbonyl, Inorganic Synthesis, 13 (1971) pp. 65-73; Baay et al., Trimethyl- and Trichlorosilylcobalt Tetracarbonyls and the Hydrosilation of Ethylene, Inorganic Chemistry, Vol. 8, No. 4 (April 1969) pp. 986-994; MacDiarmid et al., Properties of Silicon Derivates of Cobalt, Manganese, and Iron Carbonyls, Pure and Applied Chemistry (1969) Vol. 19, Issue 3, pp. 431-438; Baay et al., Synthesis and Properties of Trimethylsilyl Cobalt Tetracarbonyl and Related Compounds, Inorg. Nucl. Chem. Letters, Vol. 3 (1967) pp. 159-161).

Ethyl substituted silyl cobalt tetracarbonyl complexes ($Et_3SiCo(CO)_4$) are also disclosed in the literature (see, e.g., Sisak et al., Central European Journal of Chemistry, 4(2) (2006) p. 300). However, details of the synthesis conditions and chemical and physical properties of ethyl substituted silyl cobalt tetracarbonyl are not included in the references.

Silyl cobalt tetracarbonyl complexes ($R_3SiCo(CO)_4$), wherein R is an hydrogen (H), methyl (Me) and chlorine (Cl) are also known as precursors for cobalt-containing films (Prokap et al., nm-$Co_2Si$, CoSi, $CoSi_2$ silicide films from the single source precursor $CoSiCl_3(CO)_4$ in the presence of $SiH_4$, Thin Solid Films, 359 (2000) pp. 39-45; Kodas et al., The Chemistry of Metal CVD, Wiley-VCH (1994) Section 9.2 Classification of Precursors; Aylett et al., Chemical Vapour Deposition of Transition-Metal Silicides by Pyrolysis of Silyl Transition-Metal Carbonyl Compounds, J.C.S. Dalton (1977) pp. 2058-2061; Advances in Inorganic Chemistry and Radiochemistry, (1982) pp. 107-110).

The thermal stability of the precursor and ease of precursor synthesis are important in selecting a precursor suitable for commercial applications, as well as the final film properties of the films deposited by the precursor. $Cl_3SiCo(CO)_4$ is more stable than $H_3SiCo(CO)_4$ (Prokap et al., at 39), but Cl may cause corrosion problems in the film and in deposition facilities, such as the supply lines, chamber and exhaust line in general.

A need remains for cobalt compounds suitable for deposition of cobalt-containing films.

NOTATION AND NOMENCLATURE

Certain abbreviations, symbols, and terms are used throughout the following description and claims, and include:

As used herein, the indefinite article "a" or "an" means one or more.

As used herein, the term "alkyl group" refers to saturated functional groups containing exclusively carbon and hydrogen atoms. Further, the term "alkyl group" refers to linear, branched, or cyclic alkyl groups. Examples of linear alkyl groups include without limitation, methyl groups, ethyl groups, propyl groups, butyl groups, etc. Examples of branched alkyls groups include without limitation, t-butyl. Examples of cyclic alkyl groups include without limitation, cyclopropyl groups, cyclopentyl groups, cyclohexyl groups, etc.

As used herein, the term "hydrocarbon" means a functional group containing exclusively hydrogen and carbon atoms. The functional group may be saturated (containing only single bonds) or unsaturated (containing double or triple bonds).

As used herein, the abbreviation "Me" refers to a methyl group; the abbreviation "Et" refers to an ethyl group; the abbreviation "Pr" refers to any propyl group (i.e., n-propyl or isopropyl); the abbreviation "iPr" refers to an isopropyl group; the abbreviation "Bu" refers to any butyl group (n-butyl, iso-butyl, t-butyl, sec-butyl); the abbreviation "tBu" refers to a tert-butyl group; the abbreviation "sBu" refers to a sec-butyl group; the abbreviation "iBu" refers to an iso-butyl group; the abbreviation "Ph" refers to a phenyl group; and the abbreviation "Cp" refers to cyclopentadienyl group.

The standard abbreviations of the elements from the periodic table of elements are used herein. It should be understood that elements may be referred to by these abbreviations (e.g., Co refers to cobalt, Si refers to silicon, C refers to carbon, etc.).

SUMMARY

Compounds having one of the following formulae are disclosed:

Formula I

Formula II wherein each of $R^1$, $R^2$, $R^3$, $R^4$ and $R^5$ is independently selected from the group consisting of hydrogen and linear, cyclic, or branched hydrocarbon groups; provided that (a) $R^1 \neq R^2$ and/or $R^3$ when $R^1$ and $R^2$ and $R^3$ are a hydrocarbon group; (b) $R^1$ and $R^2$ are a hydrocarbon group when $R^3$ is H; or (c) $R^1$ is a C2-C4 hydrocarbon group when $R^2$ and $R^3$ are H. The disclosed compounds may have one or more of the following aspects:

the Formula I compound including one or two neutral adduct ligands selected from the group consisting of $NMe_3$, $NEt_3$, $NiPr_3$, $NMeEt_2$, $NC_5H_5$, $OC_4H_8$, $Me_2O$, and $Et_2O$;

$R^1 \neq R^2$ and/or $R^3$ when $R^1$ and $R^2$ and $R^3$ are a hydrocarbon group;

The compound being $Me_2EtSiCo(CO)_4$;
the compound being $Me_2iPrSiCo(CO)_4$;
the compound being $Me_2nPrSiCo(CO)_4$;
the compound being $Me_2nBuSiCo(CO)_4$;
the compound being $Me_2(sec\text{-}Bu)SiCo(CO)_4$;
the compound being $Me_2tBuSiCo(CO)_4$;
the compound being $Me_2iBuSiCo(CO)_4$;
the compound being $Me_2PhSiCo(CO)_4$;
the compound being $(CH_2\text{=}CH)Me_2SiCo(CO)_4$;
the compound being $(CH_2\text{=}CH)Et_2SiCo(CO)_4$;
$R^1$ and $R^2$ being a hydrocarbon group when $R^3$ is H;
the compound being $EtMeHSiCo(CO)_4$;
the compound being $nPrMeHSiCo(CO)_4$;
the compound being $iPrMeHSiCo(CO)_4$;
the compound being $PhMeHSiCo(C_O)_4$;
$R^1$ being a C2-C4 hydrocarbon group when $R^2$ and $R^3$ are H;
the compound being $EtH_2SiCo(CO)_4$;
the compound being $nPrH_2SiCo(CO)_4$;
the compound being $iPrH_2SiCo(CO)_4$;
the compound being $nBuH_2SiCo(CO)_4$;
the compound being $sec\text{-}BuH_2SiCo(CO)_4$;

the compound being $iBuH_2SiCo(CO)_4$;
the compound being $tBuH_2SiCo(CO)_4$;
the compound being $PhH_2SiCo(CO)_4$;
the compound being $(CH_2\text{=}CH)H_2SiCo(CO)_4$;
the compound having Formula II;
the compound being $(CO)_4CoSiH_2Co(CO)_4$;
the compound being $(CO)_4CoSiMe_2Co(CO)_4$;
the compound being $(CO)_4CoSiEt_2Co(CO)_4$;
the compound being $(CO)_4CoSi(iPr)_2Co(CO)_4$;
the compound being $(CO)_4CoSi(Ph)_2Co(CO)_4$; and
the compound being $(CO)_4CoSi(CH_2\text{=}CH)(H)Co(CO)_4$.

Methods of depositing cobalt-containing films are also disclosed. A cobalt-containing compound is introduced into a reactor having a substrate disposed therein. At least part of the cobalt-containing compound is deposited onto the substrate to form the cobalt-containing film. The cobalt-containing compound has one of the following formulae:

Formula I

Formula II wherein each of $R^1$, $R^2$, $R^3$, $R^4$, and $R^5$ is independently selected from the group consisting of hydrogen or linear, cyclic, or branched hydrocarbon groups; provided that (a) $R^1$, $R^2$, and $R^3$ are a C2 to C4 hydrocarbon when $R^1$=$R^2$=$R^3$, (b) $R^1$ and $R^2$ are a hydrocarbon group when $R^3$ is H, and (c) $R^1$ is a hydrocarbon group when $R^2$ and $R^3$ are H. The disclosed methods may have one or more of the following aspects:

the Formula I compound including one or two neutral adduct ligands selected from the group consisting of $NMe_3$, $NEt_3$, $NiPr_3$, $NMeEt_2$, $NC_5H_5$, $OC_4H_8$, $Me_2O$, and $Et_2O$;

$R^1$, $R^2$, and $R^3$ being a C2 to C4 hydrocarbon when $R^1$=$R^2$=$R^3$;

the cobalt-containing compound being $Et_3SiCo(CO)_4$;
the cobalt-containing compound being $nPr_3SiCo(CO)_4$;
the cobalt-containing compound being $iPr_3SiCo(CO)_4$;
the cobalt-containing compound being $nBu_3SiCo(CO)_4$;
the cobalt-containing compound being $sec\text{-}Bu_3SiCo(CO)_4$;
the cobalt-containing compound being $iBu_3SiCo(CO)_4$;
the cobalt-containing compound being $tBu_3SiCo(CO)_4$;
the cobalt-containing compound being $Ph_3SiCo(CO)_4$;
$R^1 \neq R^2$ and/or $R^3$ when $R^1$ and $R^2$ and $R^3$ are a hydrocarbon group;
the cobalt-containing compound being $Me_2EtSiCo(CO)_4$;
the cobalt-containing compound being $Me_2iPrSiCo(CO)_4$;
the cobalt-containing compound being $Me_2nPrSiCo(CO)_4$;
the cobalt-containing compound being $Me_2nBuSiCo(CO)_4$;
the cobalt-containing compound being $Me_2(sec\text{-}Bu)SiCo(CO)_4$;
the cobalt-containing compound being $Me_2tBuSiCo(CO)_4$;

the cobalt-containing compound being Me$_2$iBuSiCo(CO)$_4$;
the cobalt-containing compound being Me$_2$PhSiCo(CO)$_4$;
the cobalt-containing compound being Et$_2$MeSiCo(CO)$_4$;
the cobalt-containing compound being (CH$_2$=CH)Me$_2$SiCo(CO)$_4$;
the cobalt-containing compound being (CH$_2$=CH)Et$_2$SiCo(CO)$_4$;
R$^1$ and R$^2$ being a hydrocarbon group when R$^3$ is H,
the cobalt-containing compound being Me$_2$HSiCo(CO)$_4$;
the cobalt-containing compound being Et$_2$HSiCo(CO)$_4$;
the cobalt-containing compound being EtMeHSiCo(CO)$_4$;
the cobalt-containing compound being nPrMeHSiCo(CO)$_4$;
the cobalt-containing compound being iPrMeHSiCo(CO)$_4$;
the cobalt-containing compound being PhMeHSiCo(C$_O$)$_4$;
the cobalt-containing compound being Et$_2$HSiCo(CO)$_4$;
the cobalt-containing compound being nPr$_2$HSiCo(CO)$_4$;
the cobalt-containing compound being iPr$_2$HSiCo(CO)$_4$;
the cobalt-containing compound being nBu$_2$HSiCo(CO)$_4$;
the cobalt-containing compound being sec-Bu$_2$HSiCo(CO)$_4$;
the cobalt-containing compound being iBu$_2$HSiCo(CO)$_4$;
the cobalt-containing compound being tBu$_2$HSiCo(CO)$_4$;
the cobalt-containing compound being Ph$_2$HSiCo(CO)$_4$;
R$^1$ being a C2-C4 hydrocarbon group when R$^2$ and R$^3$ are H;
the cobalt-containing compound being MeH$_2$SiCo(CO)$_4$;
the cobalt-containing compound being EtH$_2$SiCo(CO)$_4$;
the cobalt-containing compound being nPrH$_2$SiCo(CO)$_4$;
the cobalt-containing compound being iPrH$_2$SiCo(CO)$_4$;
the cobalt-containing compound being nBuH$_2$SiCo(CO)$_4$;
the cobalt-containing compound being sec-BuH$_2$SiCo(CO)$_4$;
the cobalt-containing compound being iBuH$_2$SiCo(CO)$_4$;
the cobalt-containing compound being tBuH$_2$SiCo(CO)$_4$;
the cobalt-containing compound being PhH$_2$SiCo(CO)$_4$;
the cobalt-containing compound being (CH$_2$=CH)H$_2$SiCo(CO)$_4$;
the cobalt-containing compound having Formula II;
the cobalt-containing compound being (CO)$_4$CoSiH$_2$Co(CO)$_4$;
the cobalt-containing compound being (CO)$_4$CoSiMe$_2$Co(CO)$_4$;
the cobalt-containing compound being (CO)$_4$CoSiEt$_2$Co(CO)$_4$;
the cobalt-containing compound being (CO)$_4$CoSi(iPr)$_2$Co(CO)$_4$;
the cobalt-containing compound being (CO)$_4$CoSi(Ph)$_2$Co(CO)$_4$;
the cobalt-containing compound being (CO)$_4$CoSi(CH$_2$=CH)(H)Co(CO)$_4$;
The depositing step being chemical vapor deposition (CVD);
The depositing step being atomic layer deposition (ALD);
The depositing step being plasma enhanced chemical vapor deposition (PECVD);
The depositing step being plasma enhanced atomic layer deposition (PEALD);
The depositing step being pulsed chemical vapor deposition (PCVD);
The depositing step being low pressure chemical vapor deposition (LPCVD);
The depositing step being sub-atmospheric chemical vapor deposition (SACVD);
The depositing step being atmospheric pressure chemical vapor deposition (APCVD);
The depositing step being spatial ALD;
The depositing step being radicals incorporated deposition;
The depositing step being super critical fluid deposition;
The depositing step being a combination of two or more of CVD, ALD, PECVD, PEALD, PCVD, LPCVD, SACVD, APCVD, spatial ALD, radicals incorporated deposition, or super critical deposition;
the method being performed at a temperature between about 20° C. and about 800° C.;
the method being performed at a temperature between about 25° C. and about 600° C.;
the reactor having a pressure between approximately 0.1 Pa and approximately 10$^5$ Pa;
the reactor having a pressure between between approximately 2.5 Pa and approximately 10$^3$ Pa;
the cobalt-containing film being pure cobalt;
the cobalt-containing film being cobalt nitride(CoN);
the cobalt-containing film being cobalt silicide (CoSi);
the cobalt-containing film being cobalt silicide nitride (CoSiN);
the cobalt-containing film being cobalt oxide(CoO);
introducing a reaction gas into the reactor at the same time or at an alternate time as the introduction of the cobalt-containing compound;
the reaction gas being a reducing agent selected from the group consisting of N$_2$, H$_2$, NH$_3$, SiH$_4$, Si$_2$H$_6$, Si$_3$H$_8$, (Me)$_2$SiH$_2$, (C$_2$H$_5$)$_2$SiH$_2$, (CH$_3$)$_3$SiH, (C$_2$H$_5$)$_3$SiH, [N(C$_2$H$_5$)$_2$]$_2$SiH$_2$, N(CH$_3$)$_3$, N(C$_2$H$_5$)$_3$, (SiMe$_3$)$_2$NH, (CH$_3$)HNNH$_2$, (CH$_3$)$_2$NNH$_2$, phenyl hydrazine, B$_2$H$_6$, (SiH$_3$)$_3$N, radical species of these reducing agents, and mixtures of these reducing agents; and
the reaction gas being an oxidizing reagent selected from the group consisting of O$_2$, O$_3$, H$_2$O, H$_2$O$_2$, NO, NO$_2$, acetic acid, radical species of these oxidizing agents, and mixtures of these oxidizing agents.

BRIEF DESCRIPTION OF THE DRAWINGS

For a further understanding of the nature and objects for the present invention, reference should be made to the following detailed description, taken in conjunction with the accompanying drawings, in which like elements are given the same or analogous reference numbers and wherein.

DETAILED DESCRIPTION OF PREFERRED EMBODIMENTS

Cobalt-containing compounds having one of the following formulae are disclosed:

Formula I

-continued

Formula II wherein each of $R^1$, $R^2$, $R^3$ $R^4$, and $R^5$ is independently selected from Hydrogen or linear, cyclic or branched hydrocarbons; provided that (a) $R^1 \neq R^2$ and/or $R^3$ when $R^1$ and $R^2$ and $R^3$ are a hydrocarbon group; (b) $R^1$ and $R^2$ are a hydrocarbon group when $R^3$ is H; or (c) $R^1$ is a C2-C4 hydrocarbon group when $R^2$ and $R^3$ are H.

The Formula I compound may include one or two neutral adduct ligands selected from the group consisting of $NMe_3$, $NEt_3$, $NiPr_3$, $NMeEt_2$, $NC_5H_5$, $OC_4H_8$, $Me_2O$, and $Et_2O$. Preferably, the ligand is $NMe_3$ or $NEt_3$.

In one embodiment, the compound has Formula I and $R^1 \neq R^2$ and/or $R^3$ when $R^1$ and $R^2$ and $R^3$ are a hydrocarbon group. Exemplary compounds include, but are not limited to, $Me_2EtSiCo(CO)_4$, $Me_2iPrSiCo(CO)_4$, $Me_2nPrSiCo(CO)_4$, $Me_2nBuSiCo(CO)_4$, $Me_2(sec\text{-}Bu)SiCo(CO)_4$, $Me_2tBuSiCo(CO)_4$, $Me_2iBuSiCo(CO)_4$, $Me_2PhSiCo(CO)_4$, $(CH_2=CH)Me_2SiCo(CO)_4$, or $(CH_2=CH)Et_2SiCo(CO)_4$, preferably $Me_2EtSiCo(CO)_4$.

In another embodiment, the compound has Formula I and $R^1$ and $R^2$ are independently a hydrocarbon group when $R^3$ is H. Exemplary compounds include $EtMeHSiCo(CO)_4$, $nPrMeHSiCo(CO)_4$, $iPrMeHSiCo(CO)_4$, $PhMeHSiCo(C_O)_4$, $Me_2HSiCo(CO)_4$, $Et_2HSiCo(CO)_4$, $nPr_2HSiCo(CO)_4$, $iPr_2HSiCo(CO)_4$, $nBu_2HSiCo(CO)_4$, $sec\text{-}Bu_2HSiCo(CO)_4$, $iBu_2HSiCo(CO)_4$, $tBu_2HSiCo(CO)_4$, or $Ph_2HSiCo(CO)_4$, preferably $Et_2HSiCo(CO)_4$.

In another embodiment, the compound has Formula I and $R^1$ is a C2-C4 hydrocarbon group when $R^2$ and $R^3$ are H. Exemplary compounds include $EtH_2SiCo(CO)_4$, $nPrH_2SiCo(CO)_4$, $iPrH_2SiCo(CO)_4$, $nBuH_2SiCo(CO)_4$, $sec\text{-}BuH_2SiCo(CO)_4$, $iBuH_2SiCo(CO)_4$, $tBuH_2SiCo(CO)_4$, $PhH_2SiCo(CO)_4$, or $(CH_2=CH)H_2SiCo(CO)_4$, preferably $EtH_2SiCo(CO)_4$.

In yet another embodiment, the compound has Formula II. Exemplary compounds include $(CO)_4CoSiH_2Co(CO)_4$, $(CO)_4CoSiMe_2Co(CO)_4$, $(CO)_4CoSiEt_2Co(CO)_4$, $(CO)_4CoSi(iPr)_2Co(CO)_4$, $(CO)_4CoSi(Ph)_2Co(CO)_4$, or $(CO)_4CoSi(CH_2=CH)(H)Co(CO)_4$, preferably $(CO)_4CoSiH_2Co(CO)_4$, $(CO)_4CoSiMe_2Co(CO)_4$, or $(CO)_4CoSiEt_2Co(CO)_4$.

The cobalt-containing compounds may be synthesized by reacting $Co_2(CO)_8$ with an excess amount of alkylsilane at $-30°$ C. These reactants are commercially available. The mixture, with stirring, is warmed to room temperature to complete the reaction. During the reaction, hydrogen generation is observed. After 1 hour of stirring, excess alkylsilane is removed under vacuum at room temperature. The resulting dark color oil or solid is purified by vacuum distillation or sublimation.

The adduct may be synthesized by adding the cobalt-containing compound to a solvent, such as toluene or dichloromethane. The resulting mixture is cooled to approximately $-15°$ C. The adduct ligand is slowly added to the cooled mixture. The cooled adduct mixture is allowed to warm to room temperature (approximately $20°$ C.), with continuous stirring. Excess adduct ligand is removed under vacuum. The resulting adduct product may be purified by distillation or sublimation.

Methods of depositing cobalt-containing films are also disclosed. A cobalt-containing compound is introduced into a reactor having a substrate disposed therein. At least part of the cobalt-containing compound is deposited onto the substrate to form the cobalt-containing film. The cobalt-containing compound has one of the following formulae:

Formula I

Formula II wherein each of $R^1$, $R^2$, $R^3$, $R^4$, and $R^5$ is independently selected from the group consisting of hydrogen and linear, cyclic or branched hydrocarbon groups; provided that (a) $R^1$, $R^2$, and $R^3$ are a C2 to C4 hydrocarbon when $R^1=R^2=R^3$, (b) $R^1$ and $R^2$ are a hydrocarbon group when $R^3$ is H, and (c) $R^1$ is a hydrocarbon group when $R^2$ and $R^3$ are H.

The Formula I cobalt-containing compound may include one or two neutral adduct ligands selected from the group consisting of $NMe_3$, $NEt_3$, $NiPr_3$, $NMeEt_2$, $NC_5H_5$, $OC_4H_8$, $Me_2O$, and $Et_2O$. Preferably, the ligand is $NMe_3$ or $NEt_3$.

In one embodiment, the cobalt-containing compound has Formula I and $R^1$, $R^2$, and $R^3$ are a C2 to C4 hydrocarbon group when $R^1=R^2=R^3$. Exemplary cobalt-containing compounds include, but are not limited to, $Et_3SiCo(CO)_4$, $nPr_3SiCo(CO)_4$, $iPr_3SiCo(CO)_4$, $nBu_3SiCo(CO)_4$, $sec\text{-}Bu_3SiCo(CO)_4$, $iBu_3SiCo(CO)_4$, $tBu_3SiCo(CO)_4$, or $Ph_3SiCo(CO)_4$, preferably $Et_3SiCo(CO)_4$ or $iPr_3SiCo(CO)_4$.

In another embodiment, the cobalt-containing compound has Formula I and $R^1 \neq R^2$ and/or $R^3$ when $R^1$ and $R^2$ and $R^3$ are independently a hydrocarbon group. Exemplary compounds include, but are not limited to, $Me_2EtSiCo(CO)_4$, $Me_2iPrSiCo(CO)_4$, $Me_2nPrSiCo(CO)_4$, $Me_2nBuSiCo(CO)_4$, $Me_2(sec\text{-}Bu)SiCo(CO)_4$, $Me_2tBuSiCo(CO)_4$, $Me_2iBuSiCo(CO)_4$, $Me_2PhSiCo(CO)_4$, $Et_2MeSiCo(CO)_4$, $(CH_2=CH)Me_2SiCo(CO)_4$, or $(CH_2=CH)Et_2SiCo(CO)_4$, preferably $Me_2EtSiCo(CO)_4$ or $Et_2MeSiCo(CO)_4$, In another embodiment, the cobalt-containing compound has Formula I and $R^1$ and $R^2$ are a independently hydrocarbon group when $R^3$ is H. Exemplary compounds include, but are not limited to, $Me_2HSiCo(CO)_4$, $Et_2HSiCo(CO)_4$, $EtMeHSiCo(CO)_4$, $nPrMeHSiCo(CO)_4$, $iPrMeHSiCo(CO)_4$, $PhMeHSiCo(C_O)_4$, $Et_2HSiCo(CO)_4$, $nPr_2HSiCo(CO)_4$, $iPr_2HSiCo(CO)_4$, $nBu_2HSiCo(CO)_4$, $sec\text{-}Bu_2HSiCo(CO)_4$, $iBu_2HSiCo(CO)_4$, $tBu_2HSiCo(CO)_4$, or $Ph_2HSiCo(CO)_4$, preferably $Et_2HSiCo(CO)_4$, preferably $Et_2HSiCo(CO)_4$.

In another embodiment, the cobalt-containing compound has Formula I and $R^1$ is a C2-C4 hydrocarbon group when $R^2$ and $R^3$ are H. Exemplary compounds include, but are not limited to, $MeH_2SiCo(CO)_4$, $EtH_2SiCo(CO)_4$, $nPrH_2SiCo(CO)_4$, $iPrH_2SiCo(CO)_4$, $nBuH_2SiCo(CO)_4$, $sec\text{-}BuH_2SiCo(CO)_4$, $iBuH_2SiCo(CO)_4$, $tBuH_2SiCo(CO)_4$, $PhH_2SiCo(CO)_4$, or $(CH_2=CH)H_2SiCo(CO)_4$, preferably $EtH_2SiCo(CO)_4$.

In yet another embodiment, the cobalt-containing compound has Formula II. Exemplary compounds include, but are not limited to $(CO)_4CoSiH_2Co(CO)_4$, $(CO)_4CoSiMe_2Co(CO)_4$, $(CO)_4CoSiEt_2Co(CO)_4$, $(CO)_4CoSi(iPr)_2Co(CO)_4$, $(CO)_4CoSi(Ph)_2Co(CO)_4$, or $(CO)_4CoSi(CH_2=CH)(H)Co(CO)_4$, preferably $(CO)_4CoSiH_2Co(CO)_4$, $(CO)_4CoSiMe_2Co(CO)_4$, or $(CO)_4CoSiEt_2Co(CO)_4$.

At least part of the disclosed cobalt-containing compounds may deposited onto a substrate to form the cobalt-containing films by chemical vapor deposition (CVD), atomic layer deposition (ALD), or other types of depositions that are related to vapor coating such as a plasma enhanced CVD (PECVD), plasma enhanced ALD (PEALD), pulsed CVD (PCVD), low pressure CVD (LPCVD), sub-atmospheric CVD (SACVD) or atmospheric pressure CVD (APCVD), hot-wire CVD (HWCVD, also known as catCVD, in which a hot wire serves as a catalyst for the deposition process), spatial ALD, hot-wire ALD (HWALD), radicals incorporated deposition, and super critical fluid deposition or combinations thereof. Preferably, the deposition method is CVD, ALD, or PE-ALD.

The disclosed methods may be useful in the manufacture of semiconductor, photovoltaic, LCD-TFT, or flat panel type devices. The method includes introducing the vapor of at least one Co-containing compound disclosed above into a reactor having at least one substrate disposed therein and depositing at least part of the cobalt-containing compound onto the at least one substrate to form a cobalt-containing layer using a vapor deposition process. The temperature and the pressure within the reactor and the temperature of the substrate are held at conditions suitable for formation of the Co-containing layer on at least one surface of the substrate. A reaction gas may also be used to help in formation of the Co-containing layer.

The disclosed methods may also be used to form a two element-containing layer on a substrate using a vapor deposition process and, more particularly, for deposition of $CoMO_x$ layers, wherein M is the second element and is selected from the group consisting of group 2, group 13, group 14, transition metal, lanthanides, and combinations thereof, and more preferably from Mg, Ca, Sr, Ba, Hf, Nb, Ta, Al, Si, Ge, Y, or lanthanides. The method includes: introducing at least one Co-containing compound disclosed above into a reactor having at least one substrate disposed therein, introducing a second precursor into the reactor, and depositing at least part of the cobalt-containing compound and at least part of the second precursor onto the at least one substrate to form the two element-containing layer using a vapor deposition process.

The reactor may be any enclosure or chamber of a device in which deposition methods take place, such as, without limitation, a parallel-plate type reactor, a cold-wall type reactor, a hot-wall type reactor, a single-wafer reactor, a multi-wafer reactor, or other such types of deposition systems. All of these exemplary reactors are capable of serving as an ALD or CVD reactor. The reactor may be maintained at a pressure ranging from about 0.5 mTorr to about 20 Torr. In addition, the temperature within the reactor may range from about room temperature (20° C.) to about 600° C. One of ordinary skill in the art will recognize that the temperature may be optimized through mere experimentation to achieve the desired result.

The temperature of the reactor may be controlled by either controlling the temperature of the substrate holder (called a cold wall reactor) or controlling the temperature of the reactor wall (called a hot wall reactor) or a combination of both methods. Devices used to heat the substrate are known in the art.

The reactor wall may be heated to a sufficient temperature to obtain the desired film at a sufficient growth rate and with desired physical state and composition. A non-limiting exemplary temperature range to which the reactor wall may be heated includes from approximately 20° C. to approximately 600° C. When a plasma deposition process is utilized, the deposition temperature may range from approximately 20° C. to approximately 550° C. Alternatively, when a thermal process is performed, the deposition temperature may range from approximately 100° C. to approximately 600° C.

Alternatively, the substrate may be heated to a sufficient temperature to obtain the desired cobalt-containing layer at a sufficient growth rate and with desired physical state and composition. A non-limiting exemplary temperature range to which the substrate may be heated includes from 100° C. to 600° C. Preferably, the temperature of the substrate remains less than or equal to 500° C.

The type of substrate upon which the cobalt-containing layer will be deposited will vary depending on the final use intended. In some embodiments, the substrate may be chosen from oxides which are used as dielectric materials in MIM, DRAM, or FeRam technologies (for example, $ZrO_2$ based materials, $HfO_2$ based materials, $TiO_2$ based materials, rare earth oxide based materials, ternary oxide based materials, etc.) or from nitride-based layers (for example, TaN) that are used as an oxygen barrier between copper and the low-k layer. Other substrates may be used in the manufacture of semiconductors, photovoltaics, LCD-TFT, or flat panel devices. Examples of such substrates include, but are not limited to, solid substrates such as copper and copper based alloys like CuMn, metal nitride-containing substrates (for example, TaN, TiN, WN, TaCN, TiCN, TaSiN, and TiSiN); insulators (for example, $SiO_2$, $Si_3N_4$, SiON, $HfO_2$, $Ta_2O_5$, $ZrO_2$, $TiO_2$, $Al_2O_3$, and barium strontium titanate); or other substrates that include any number of combinations of these materials. The actual substrate utilized may also depend upon the specific compound embodiment utilized. In many instances though, the preferred substrate utilized will be selected from Si and $SiO_2$ substrates.

The disclosed cobalt-containing compounds may be supplied either in neat form or in a blend with a suitable solvent, such as ethyl benzene, xylene, mesitylene, decane, dodecane, to form a precursor mixture. The disclosed compounds may be present in varying concentrations in the solvent.

One or more of the neat compounds or precursor mixtures are introduced into a reactor in vapor form by conventional means, such as tubing and/or flow meters. The vapor form of the neat compound or precursor mixture may be produced by vaporizing the neat compound or precursor mixture through a conventional vaporization step such as direct vaporization, distillation, by bubbling, or by using a sublimator such as the one disclosed in PCT Publication WO2009/087609 to Xu et al. The neat compound or precursor mixture may be fed in liquid state to a vaporizer where it is vaporized before it is introduced into the reactor. Alternatively, the neat compound or precursor mixture may be vaporized by passing a carrier gas into a container containing the neat compound or precursor mixture or by bubbling the carrier gas into the neat compound or precursor mixture. The carrier gas may include, but is not limited to, Ar, He, $N_2$, and mixtures thereof. The carrier gas and compound are then introduced into the reactor as a vapor.

If necessary, the container of the neat compound or precursor mixture may be heated to a temperature that permits the neat compound or precursor mixture to be in its liquid phase and to have a sufficient vapor pressure. The container may be maintained at temperatures in the range of, for example, approximately 0° C. to approximately 200° C. Those skilled in the art recognize that the temperature of the container may be adjusted in a known manner to control the amount of precursor vaporized.

In addition to the optional mixing of the cobalt-containing compound with solvents, second precursors, and stabilizers prior to introduction into the reactor, the cobalt-containing compound may be mixed with a reaction gas inside the reactor. Exemplary reaction gases include, without limitation, second precursors such as transition metal-containing precursors (eg. Niobium), rare earth-containing precursors, strontium-containing precursors, barium-containing precursors, aluminum-containing precursors such as TMA, and any combination thereof. These or other second precursors may be incorporated into the resultant layer in small quantities, as a dopant, or as a second or third metal in the resulting layer, such as $CoMO_x$.

The reaction gas may include a reducing reagent which is selected from, but not limited to, $N_2$, $H_2$, $NH_3$, $SiH_4$, $Si_2H_6$, $Si_3H_8$, $(Me)_2SiH_2$, $(C_2H_5)_2SiH_2$, $(CH_3)_3SiH$, $(C_2H_5)_3SiH$, $[N(C_2H_5)_2]_2SiH_2$, $N(CH_3)_3$, $N(C_2H_5)_3$, $(SiMe_3)_2NH$, $(CH_3)HNNH_2$, $(CH_3)_2NNH_2$, phenyl hydrazine, $B_2H_6$, $(SiH_3)_3N$, radical species of these reducing agents, and mixtures of these reducing agents. Preferably, when an ALD process is performed, the reducing reagent is $H_2$.

When the desired cobalt-containing layer also contains oxygen, such as, for example and without limitation, $CoO_x$ and $CoMO_x$, the reaction gas may include an oxidizing reagent which is selected from, but not limited to, $O_2$, $O_3$, $H_2O$, $H_2O_2$, acetic acid, formalin, para-formaldehyde, radical species of these oxidizing agents, and mixtures of these oxidizing agents. Preferably, when an ALD process is performed, the oxidizing reagent is $H_2O$.

The reaction gas may be treated by plasma in order to decompose the reaction gas into its radical form. The plasma may be generated or present within the reaction chamber itself. Alternatively, the plasma may generally be at a location removed from the reaction chamber, for instance, in a remotely located plasma system. One of skill in the art will recognize methods and apparatus suitable for such plasma treatment.

For example, the reaction gas may be introduced into a direct plasma reactor, which generates plasma in the reaction chamber, to produce the plasma-treated reaction gas in the reaction chamber. Exemplary direct plasma reactors include the Titan™ PECVD System produced by Trion Technologies. The reaction gas may be introduced and held in the reaction chamber prior to plasma processing. Alternatively, the plasma processing may occur simultaneously with the introduction of the reaction gas. In-situ plasma is typically a 13.56 MHz RF capacitively coupled plasma that is generated between the showerhead and the substrate holder. The substrate or the showerhead may be the powered electrode depending on whether positive ion impact occurs. Typical applied powers in in-situ plasma generators are from approximately 50 W to approximately 1000 W. The disassociation of the reaction gas using in-situ plasma is typically less than achieved using a remote plasma source for the same power input and is therefore not as efficient in reaction gas disassociation as a remote plasma system, which may be beneficial for the deposition of metal-nitride-containing films on substrates easily damaged by plasma.

Alternatively, the plasma-treated reaction gas may be produced outside of the reaction chamber. The MKS Instruments' ASTRONi® reactive gas generator may be used to treat the reaction gas prior to passage into the reaction chamber. Operated at 2.45 GHz, 7 kW plasma power, and a pressure ranging from approximately 3 Torr to approximately 10 Torr, the reaction gas $O_2$ may be decomposed into two $O^-$ radicals. Preferably, the remote plasma may be generated with a power ranging from about 1 kW to about 10 kW, more preferably from about 2.5 kW to about 7.5 kW.

When the desired cobalt-containing layer also contains another element, such as, for example and without limitation, Nb, Sr, Ba, Al, Ta, Hf, Nb, Mg, Y, Ca, As, Sb, Bi, Sn, Pb, Mn, lanthanides (such as Er), or combinations thereof, the reaction gas may include a second precursor which is selected from, but not limited to, metal alkyls, such as $(Me)_3Al$, metal amines, such as $Nb(Cp)(NtBu)(NMe_2)_3$, and any combination thereof.

The cobalt-containing compound and one or more reaction gases may be introduced into the reactor simultaneously (chemical vapor deposition), sequentially (atomic layer deposition), or in other combinations. For example, the cobalt-containing compound may be introduced in one pulse and two additional precursors may be introduced together in a separate pulse [modified atomic layer deposition]. Alternatively, the reactor may already contain the reaction gas prior to introduction of the cobalt-containing compound. Alternatively, the cobalt-containing compound may be introduced to the reactor continuously while other reaction gases are introduced by pulse (pulsed-chemical vapor deposition). The reaction gas may be passed through a plasma system localized or remotely from the reactor, and decomposed to radicals. In each example, a pulse may be followed by a purge or evacuation step to remove excess amounts of the component introduced. In each example, the pulse may last for a time period ranging from about 0.01 s to about 30 s, alternatively from about 0.3 s to about 3 s, alternatively from about 0.5 s to about 2 s. In another alternative, the cobalt-containing compound and one or more reaction gases may be simultaneously sprayed from a shower head under which a susceptor holding several wafers is spun (spatial ALD).

In one non-limiting exemplary atomic layer deposition type process, the vapor phase of a cobalt-containing compound is introduced into the reactor, where it is contacted with a suitable substrate. Excess cobalt-containing compound may then be removed from the reactor by purging and/or evacuating the reactor. An oxidizing reagent is introduced into the reactor where it reacts with the absorbed cobalt-containing compound in a self-limiting manner. Any excess oxidizing reagent is removed from the reactor by purging and/or evacuating the reactor. If the desired layer is a cobalt oxide layer, this two-step process may provide the desired layer thickness or may be repeated until a layer having the necessary thickness has been obtained.

Alternatively, if the desired CoO layer contains a second element (i.e., $CoMO_x$), the two-step process above may be followed by introduction of the vapor of a second precursor into the reactor. The second precursor will be selected based on the nature of the $CoMO_x$ layer being deposited. After introduction into the reactor, the second precursor is contacted with the substrate. Any excess second precursor is removed from the reactor by purging and/or evacuating the reactor. Once again, an oxidizing reagent may be introduced into the reactor to react with the second precursor. Excess oxidizing reagent is removed from the reactor by purging and/or evacuating the reactor. If a desired layer thickness has been achieved, the process may be terminated. However, if a thicker layer is desired, the entire four-step process may be repeated. By alternating the provision of the cobalt-containing compound, second precursor, and oxidizing reagent, a $CoMO_x$ layer of desired composition and thickness may be deposited.

Additionally, by varying the number of pulses, layers having a desired stoichiometric M:Co ratio may be obtained.

For example, a $CoMO_2$ layer may be obtained by having one pulse of the cobalt-containing compound and one pulse of the second precursor, with each pulse being followed by pulses of the oxidizing reagent. However, one of ordinary skill in the art will recognize that the number of pulses required to obtain the desired layer may not be identical to the stoichiometric ratio of the resulting layer.

The cobalt-containing layers resulting from the processes discussed above may include pure cobalt, cobalt nitride (CoN), cobalt silicide (CoSi), cobalt silicide nitride (CoSiN), and cobalt oxide(CoO). One of ordinary skill in the art will recognize that by judicial selection of the appropriate cobalt-containing compound and reaction gases, the desired Co-containing layer composition may be obtained.

Upon obtaining a desired film thickness, the film may be subject to further processing, such as thermal annealing, furnace-annealing, rapid thermal annealing, UV or e-beam curing, and/or plasma gas exposure. Those skilled in the art recognize the systems and methods utilized to perform these additional processing steps. For example, the cobalt-containing film may be exposed to a temperature ranging from approximately 200° C. to approximately 1000° C. for a time ranging from approximately 0.1 second to approximately 7200 seconds under an inert atmosphere, a H-containing atmosphere, a N-containing atmosphere, an O-containing atmosphere, or combinations thereof. Most preferably, the temperature is 400° C. for 3600 seconds under a H-containing atmosphere. The resulting film may contain fewer impurities and therefore may have an improved density resulting in improved leakage current. The annealing step may be performed in the same reaction chamber in which the deposition process is performed. Alternatively, the substrate may be removed from the reaction chamber, with the annealing/flash annealing process being performed in a separate apparatus. Any of the above post-treatment methods, but especially thermal annealing, is expected to effectively reduce any carbon and nitrogen contamination of the cobalt-containing film. This in turn is expected to improve the resistivity of the film.

In another alternative, the disclosed cobalt-containing compounds may be used as doping or implantation agents. Part of the disclosed cobalt-containing compound may be deposited on top of the film to be doped, such as an indium arsenide (InAs) film, a gallium arsenide (GaAs) film, a zinc oxide (ZnO) film, a titanium oxide film, a copper oxide film, or a tin dioxide ($SnO_2$) film. The cobalt then diffuses into the film during an annealing step to form the cobalt-doped films {(In,Co)As, (Ga,Co)As, (Co)ZnO, (Co)TiO, (Co)CuO, or (Co)$SnO_2$}. See, e.g., US2008/0241575 to Lavoie et al., the doping method of which is incorporated herein by reference in its entirety. Alternatively, high energy ion implantation using a variable energy radio frequency quadrupole implanter may be used to dope the cobalt of the cobalt-containing compound into a film. See, e.g., Kensuke et al., JVSTA 16(2) March/April 1998, the implantation method of which is incorporated herein by reference in its entirety. In another alternative, plasma doping, pulsed plasma doping or plasma immersion ion implantation may be performed using the disclosed cobalt-containing compounds. See, e.g., Felch et al., Plasma doping for the fabrication of ultra-shallow junctions Surface Coatings Technology, 156 (1-3) 2002, pp. 229-236, the doping method of which is incorporated herein by reference in its entirety.

EXAMPLES

The following non-limiting examples are provided to further illustrate embodiments of the invention. However, the examples are not intended to be all inclusive and are not intended to limit the scope of the inventions described herein.

Example 1

Figure 1:
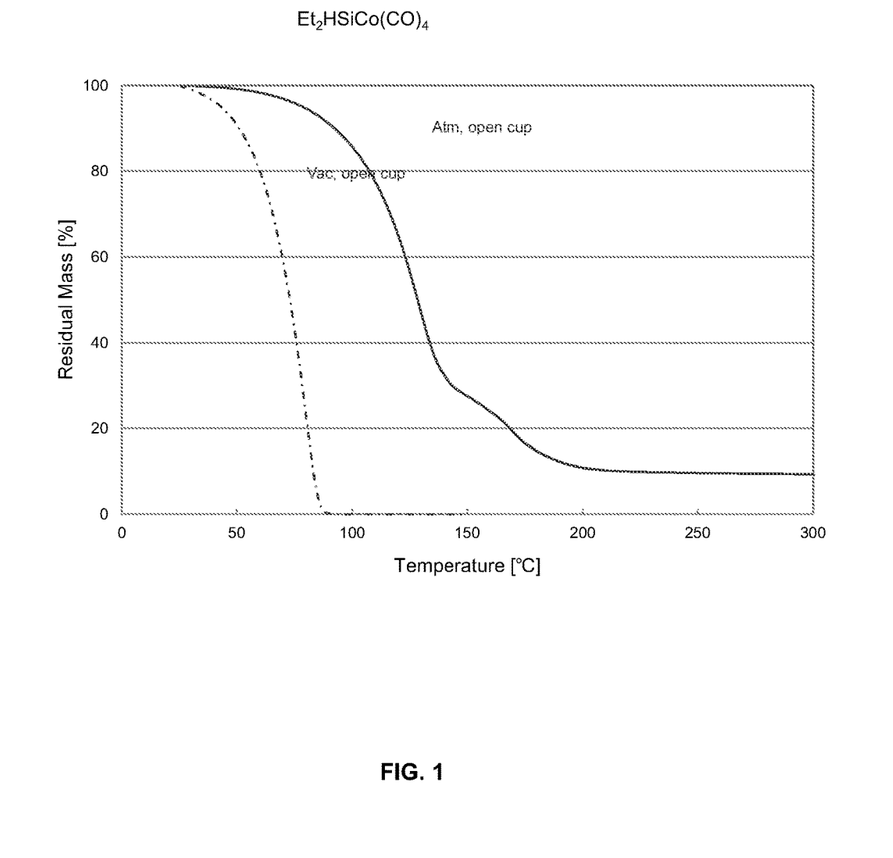
FIG. 1 is a thermogravimetric (TGA) graph demonstrating the % residual mass with temperature change of Et$_2$HSiCo(CO)$_4$.

Synthesis of $(CO)_4CoSi(H)Et_2$ $Co_2(CO)_8$ (5.88 g, 17.2 mmol) was added to a 100 mL flask. Liquid $SiH_2Et_2$ (15.2 g, 172 mmol) was slowly dropped into the flask at −30° C. The mixture was allowed to warm to room temperature with continuous stirring to complete reaction. Hydrogen gas was generated after 5 min stirring. After 1 hour of stirring, excess $SiH_2Et_2$ was removed as a gas under vacuum at room temperature. The product was purified by distillation under vacuum. Yellow liquid was obtained (2.65 g (10.26 mmol), 60% yield). As shown by the dotted line in FIG. 1, less than 1% residue was produced in ThermoGravimetric Analysis (TGA) under vacuum (20 mbar) open cup conditions. The solid line in FIG. 1 shows the results under atmospheric (1010 mbar) open cup conditions.

1H NMR (δ, $C_6D_6$) 1.0 (m, 10H, —$CH_2$ and —$CH_3$), 4.6 (m, 1H).

Figure 4:
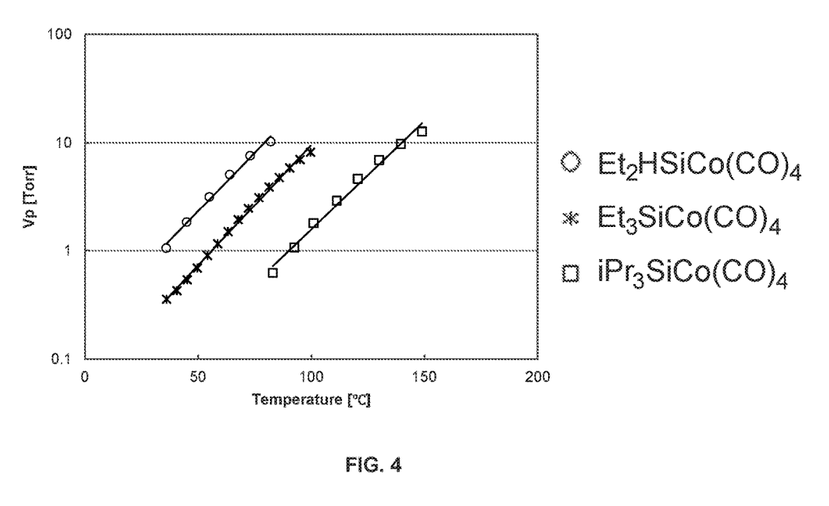
FIG. 4 is a graph of the vapor pressure (Torr) with temperature change.

Vapor pressure=1 Torr/36° C. (see FIG. 4), decomposition point=137° C. No melting/freezing points were observed between −100~+30° C. by Differential Scanning calorimetry (DSC).

Example 2

Figure 2:
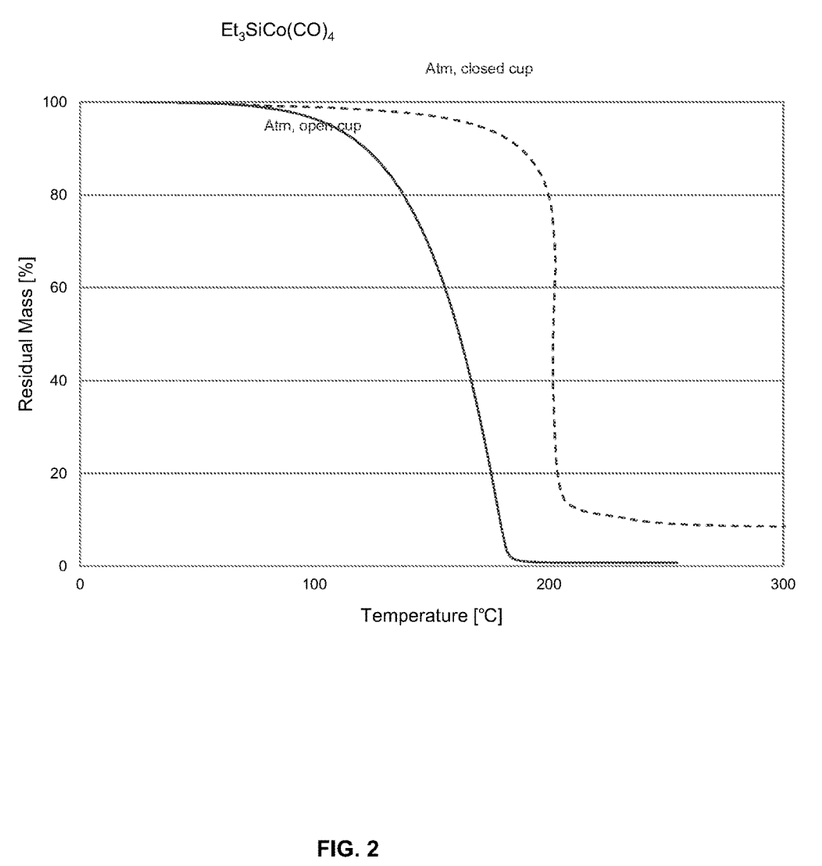
FIG. 2 is a TGA graph demonstrating the % residual mass with temperature change of Et$_3$SiCo(CO)$_4$.

Synthesis of $(CO)_4CoSiEt_3$ $Co_2(CO)_8$ (2 g, 5.85 mmol) was added to a 100 mL of flask in the same manner as in Example 1. Liquid $SiHEt_3$ (9.32 g, 80 mmol) was slowly dropped into the flask at −30° C. The mixture was allowed to warm to room temperature with continuous stirring to complete reaction. Hydrogen gas was generated during stirring. After 1 hour stirring, excess $SiHEt_3$ was removed as a gas under vacuum at room temperature. The product was purified by distillation under vacuum. Brown liquid was obtained (2.5 g (8.73 mmol), 75% yield). As shown by the solid line in FIG. 2, less than 1% residue was produced in ThermoGravimetric Analysis (TGA) under atmospheric open cup conditions. The dotted line in FIG. 2 shows the results under atmospheric closed cup conditions.

1H NMR (δ, $C_6D_6$) 0.94 (q, 6H, Si—$CH_2$), 0.99 (t, 9H, —$CH_3$).

Vapor pressure=1 Torr/57° C. (see FIG. 4), decomposition point=203° C., melting point=−9° C., freezing point=−31° C. by DSC.

Example 3

Figure 3:
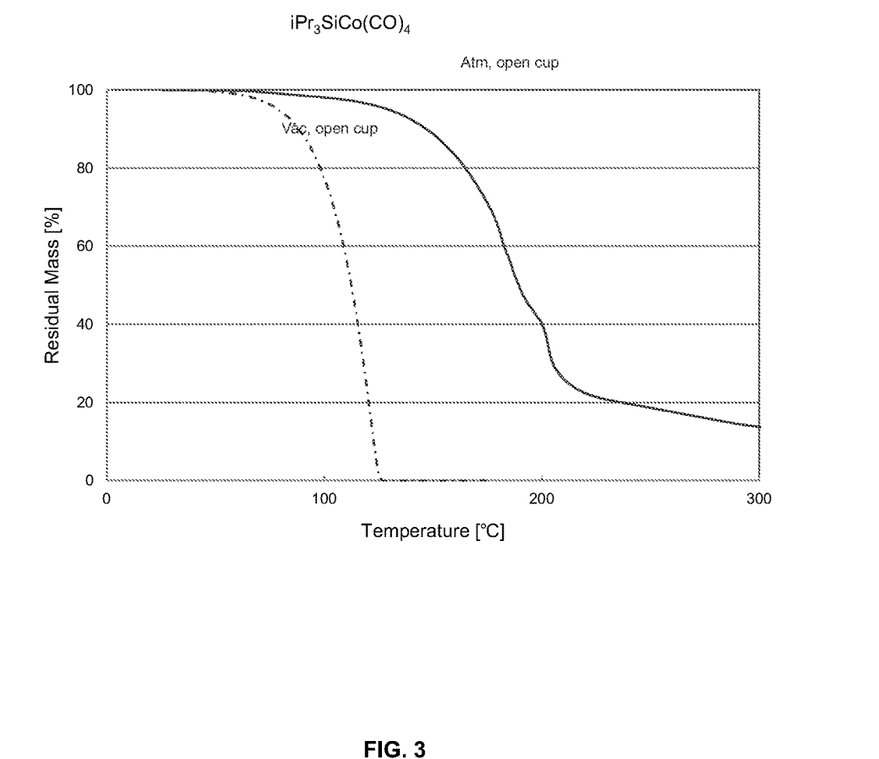
FIG. 3 is a TGA graph demonstrating the % residual mass with temperature change of iPr$_3$SiCo(CO)$_4$.

Synthesis of $(CO)_4CoSi(iPr)_3$ $Co_2(CO)_8$ (5 g, 14.6 mmol) was added to a 100 mL of flask in the same manner as in Example 1. Liquid Si(H)i$Pr_3$ (925 g, 58.4 mmol) was slowly dropped into the flask at −30° C. The mixture was allowed to warm to room temperature with continuous stirring to complete reaction. Hydrogen gas was generated during stirring. After 1 hour stirring, excess Si(H)i$Pr_3$ was removed as a gas under vacuum at room temperature. The product was purified by distillation under vacuum. Brown liquid was obtained (5.6 g (16.9 mmol), 58% yield). As shown by the dotted line in FIG. 3, less than 1% residue was produced in ThermoGravimetric Analysis (TGA) under vacuum open cup conditions. The solid line in FIG. 3 shows the results under atmospheric open cup conditions.

1H NMR (δ, $C_6D_6$) 1.12 (d, 18H, —$CH_3$), 1.42 (m, 3H, —CH).

Vapor pressure=1 Torr/92° C. (see FIG. 4), decomposition point=176° C., melting point=51° C. by DSC.

Example 4

Synthesis of $(CO)_4CoSi(Et_2)Co(CO)_4$ $Co_2(CO)_8$ (5.88 g, 17.2 mmol) was added to a 100 mL flask. Liquid $SiH_2Et_2$ (15.2 g, 172 mmol) was slowly dropped into the flask at −30° C. The mixture was allowed to warm to room temperature with continuous stirring to complete reaction. Hydrogen gas was generated after 5 min stirring. After 1 hour of stirring, excess $SiH_2Et_2$ was removed as a gas under vacuum at room temperature. This method is the same method used to synthesize $(CO)_4CoSi(H)Et_2$ in Example 1 above. $(CO)_4CoSi(Et_2)Co(CO)_4$ was also produced.

Example 5

Comparison of Silyl Cobalt Tetracarbonyl Compounds

As shown in Table 1, below, $Me_3SiCo(CO)_4$ is a solid at room temperature having a melting point of 75° C. and $Et_3SiCo(CO)_4$ and $Et_2HSiCo(CO)_4$ are liquids at room temperature. In general a precursor is delivered to deposition chamber as gas or vapor by vacuuming or bubbling with inert gas. Being liquid at room temperature provides a strong advantage, especially for precursors which have low decomposition point, such as decomposition points below 200° C. During the delivery, excess heating which may cause precursor decomposition is undesirable. Additionally, liquid precursors enable use of liquid level sensors in the precursor canister, liquid delivery systems, and easier transfill.

TABLE 1

Comparison of silyl cobalt tetracarbonyl $R_3SiCo(CO)_4$

| @ 20° C. | $R_3 = Me_3$ Solid | $R_3 = Cl_3$ Solid | $R_3 = Et_3$ Liquid | $R_3 = iPr_3$ Solid | $R_3 = Et_2H$ Liquid |
|---|---|---|---|---|---|
| Melting point [° C.] | 75 | ND | −9 | 51 | <−100 |
| Freezing point [° C.] | ND | ND | −30 | — | <−100 |
| Vapor pressure | ND | 29° C./ 1 Torr* | 57° C./ 1 Torr | 92° C./ 1 Torr | 36° C./ 1 Torr |
| Decomposition point [° C.] | <200 | <200 | 203 | 176 | 137 |
| ΔH [kJ/mol] | | 40.95* (lit) | 49.4 | 57.8 | 45.6 |

*Calculated value according to literature (Prokap et al. Thin Solid Films, 359 (2000) pp. 39-45).

Example 6

Pyrolysis Test

The temperature effect on the compound of Example 2 ($Et_3SiCo(CO)_4$).

The molecule was introduced into a chamber containing a $SiO_2$ wafer. The chamber was held at a pressure of 4.3 Torr. The temperature of the chamber varies from 150° C. to 250° C. After 30 minutes, too thin of a film was deposited onto the $SiO_2$ wafer at 150° C. for in-house analysis. Thermal decomposition of the molecule occurred at 200° C. resulting in a thin film forming on the $SiO_2$ wafer. Co films were formed using $H_2$ and $NH_3$ as a reactant in TCVD processes at temperature of 200° C., 225° C.-250° C., and 350° C., and a chamber pressure of 6.2 Torr. The resulting Co films had high concentrations of C and O. Depositions using $NH_3$ results in N contamination. Depositions using $H_2$ at lower temperatures resulted in lower C concentrations in the films.

Example 7

Prophetic Synthesis of $Et_3SiCo(CO)_4 \cdot 2NEt_3$ $Et_3SiCo(CO)_4$ will be added to a 100 mL flask with toluene or dichloromethane. The solution will be cooled at −15° C. and liquid triethylamine will be added slowly. After addition of the amine, the mixture will be allowed to warm to room temperature with continuous stirring to complete reaction. After overnight reaction, excess triethylamine will be removed under vacuum. The product may be purified by distillation or sublimation under vacuum.

Example 8

Prophetic Synthesis of $(CO)_4CoSi(Et)Me_2$ $Co_2(CO)_8$ will be added to a 100 mL flask. Liquid $SiHEtMe_2$ will slowly be dropped into the flask at −30° C. The mixture will be allowed to warm to room temperature with continuous stirring to complete reaction. Hydrogen gas will be generated after 5 min stirring. After 1 hour of stirring, excess $SiHEtMe_2$ will be removed as a gas under vacuum at room temperature. The product may be purified by distillation under vacuum.

Example 9

Prophetic Synthesis of $(CH_2$=$CH)H_2SiCo(CO)_4$ $Co_2(CO)_8$ will be added to a 100 mL flask. Liquid $SiH_3(CH_2$=$CH)$ will slowly be dropped into the flask at −30° C. The mixture will be allowed to warm to room temperature with continuous stirring to complete reaction. Hydrogen gas will be generated after 5 min stirring. After 1 hour of stirring, excess $SiH_3(CH_2$=$CH)$ will be removed as a gas under vacuum at room temperature. The product may be purified by distillation under vacuum.

Example 10

Prophetic ALD Deposition of Co Film

Applicants believe that any of the disclosed $R_3SiCo(CO)_4$ compounds, may be used to deposit Co films using ALD techniques known in the art and $H_2$ as a reaction gas.

Example 11

Prophetic ALD Deposition of CoO Film

Applicants believe that any of the disclosed $R_3SiCo(CO)_4$ compounds may be used to deposit CoO films using ALD techniques known in the art and $H_2O$ or $O_3$ or $O_2$ as a reaction gas.

Example 12

Prophetic ALD Deposition of CoN Film

Applicants believe that any of the disclosed $R_3SiCo(CO)_4$ compounds may be used to deposit CoN films using ALD techniques known in the art and $NH_3$ as a reaction gas.

Example 13

Prophetic ALD Deposition of CoSi Film

Applicants believe that any of the disclosed $R_3SiCo(CO)_4$ compounds may be used to deposit CoSi films using ALD techniques known in the art and $H_2$ as a reaction gas.

Example 14

Prophetic ALD Deposition of CoSiN Film

Applicants believe that any of the disclosed $R_3SiCo(CO)_4$ compounds may be used to deposit CoSiN films using ALD techniques known in the art and $H_2$ and $NH_3$ as reaction gases.

It will be understood that many additional changes in the details, materials, steps, and arrangement of parts, which have been herein described and illustrated in order to explain the nature of the invention, may be made by those skilled in the art within the principle and scope of the invention as expressed in the appended claims. Thus, the present invention is not intended to be limited to the specific embodiments in the examples given above and/or the attached drawings.

We claim:

1. A method of depositing a cobalt-containing film, the method comprising:
    introducing a cobalt-containing compound into a reactor having a substrate disposed therein, wherein the cobalt-containing compound has one of the following formulae:

Formula I

Formula II wherein each of $R^1$, $R^2$, $R^3$, $R^4$, and $R^5$ is independently selected from the group consisting of hydrogen and linear, cyclic, or branched hydrocarbon groups; provided that (a) $R^1$, $R^2$, and $R^3$ are a C2 to C4 hydrocarbon when $R^1=R^2=R^3$, (b) $R^1$ and $R^2$ are a hydrocarbon group when $R^3$ is H, or (c) $R^1$ is a hydrocarbon group when $R^2$ and $R^3$ are H; and
    depositing at least part of the cobalt-containing compound onto the substrate to form the cobalt-containing film.

2. The method of claim 1, wherein the Formula I compound includes one or two neutral adduct ligands selected from the group consisting of $NMe_3$, $NEt_3$, $NiPr_3$, $NMeEt_2$, $NC_5H_5$, $OC_4H_8$, $Me_2O$, and $Et_2O$.

3. The method of claim 1, wherein the cobalt-containing compound is selected from the group consisting of $Et_3SiCo(CO)_4$, $nPr_3SiCo(CO)_4$, $iPr_3SiCo(CO)_4$, $nBu_3SiCo(CO)_4$, $sec$-$Bu_3SiCo(CO)_4$, $iBu_3SiCo(CO)_4$, $tBu_3SiCo(CO)_4$, $EtMeHSiCo(CO)_4$, $nPrMeHSiCo(CO)_4$, $iPrMeHSiCo(CO)_4$, $PhMeHSiCo(Co)_4$, $Me_2HSiCo(CO)_4$, $Me_2iPrSiCo(CO)_4$, $Me_2nPrSiCo(CO)_4$, $Me_2nBuSiCo(CO)_4$, $Me_2(sec$-$Bu)SiCo(CO)_4$, $Me_2tBuSiCo(CO)_4$, $Me_2iBuSiCo(CO)_4$, $Me_2PhSiCo(CO)_4$, $Me_2HSiCo(CO)_4$, $Et_2HSiCo(CO)_4$, $Et_2MeSiCo(CO)_4$, $nPr_2HSiCo(CO)_4$, $iPr_2HSiCo(CO)_4$, $nBu_2HSiCo(CO)_4$, $sec$-$Bu_2HSiCo(CO)_4$, $iBu_2HSiCo(CO)_4$, $tBu_2HSiCo(CO)_4$, $Ph_2HSiCo(CO)_4$, $MeH_2SiCo(CO)_4$, $EtH_2SiCo(CO)_4$, $nPrH_2SiCo(CO)_4$, $iPrH_2SiCo(CO)_4$, $nBuH_2SiCo(CO)_4$, $sec$-$BuH_2SiCo(CO)_4$, $iBUH_2SiCo(CO)_4$, $tBUH_2SiCo(CO)_4$, $PhH_2SiCo(CO)_4$, $(CO)_4CoSiH_2Co(CO)_4$, $(CO)_4CoSiMe_2Co(CO)_4$, $(CO)_4CoSiEt_2Co(CO)_4$, $(CO)_4CoSi(iPr)_2Co(CO)_4$, $(CO)_4CoSi(Ph)_2Co(CO)_4$, and $(CO)_4CoSi(CH_2=CH)(H)Co(CO)_4$.

4. The method of claim 3, wherein the cobalt containing compound is selected from the group consisting of $Et_2HSiCo(CO)_4$, $Et_3SiCo(CO)_4$, and $iPrH_3SiCo(CO)_4$.

5. The method of claim 4, wherein the cobalt containing compound is $Et_3SiCo(CO)_4$.

6. The method of claim 1, wherein the depositing step is selected from the group consisting of chemical vapor deposition (CVD), atomic layer deposition (ALD), plasma enhanced chemical vapor deposition (PECVD), plasma enhanced atomic layer deposition (PEALD), pulsed chemical vapor deposition (PCVD), low pressure chemical vapor deposition (LPCVD), sub-atmospheric chemical vapor deposition (SACVD), atmospheric pressure chemical vapor deposition (APCVD), spatial ALD, radicals incorporated deposition, super critical fluid deposition, and combinations thereof.

7. The method of claim 1, wherein the method is performed at a temperature between 20° C. and 800° C.

8. The method of claim 1, wherein the reactor has a pressure between 0.1 Pa and $10^5$ Pa.

9. The method of claim 1, wherein the cobalt-containing film is selected from the group consisting of pure cobalt, cobalt nitride(CoN), cobalt silicide (CoSi), cobalt silicide nitride (CoSiN), and cobalt oxide(CoO).

10. The method of claim 1, further comprising introducing a reaction gas into the reactor at the same time or at an alternate time as the introduction of the cobalt-containing compound.

11. The method of claim 10, wherein the reaction gas is a reducing agent selected from the group consisting of $N_2$, $H_2$, $NH_3$, $SiH_4$, $Si_2H_6$, $Si_3H_8$, $(Me)_2SiH_2$, $(C_2H_5)_2SiH_2$, $(CH_3)_3SiH$, $(C_2H_5)_3SiH$, $[N(C_2H_5)_2]_2SiH_2$, $N(CH_3)_3$, $N(C_2H_5)_3$, $(SiMe_3)_2NH$, $(CH_3)HNNH_2$, $(CH_3)_2NNH_2$, phenyl hydrazine, $B_2H_6$, $(SiH_3)_3N$, radical species of these reducing agents, and mixtures of these reducing agents.

12. The method of claim 10, wherein the reaction gas is an oxidizing reagent selected from the group consisting of $O_2$, $O_3$, $H_2O$, $H_2O_2$, NO, $NO_2$, acetic acid, radical species of these oxidizing agents, and mixtures of these oxidizing agents.

13. A method of depositing a cobalt-containing film, the method comprising:
    introducing a cobalt-containing compound into a reactor having a substrate disposed therein, wherein the cobalt-containing compound has the following formula:

Formula I wherein each of $R^1$, $R^2$, and $R^3$ is independently selected from the group consisting of hydrogen and linear, cyclic, or branched hydrocarbon groups; provided that (a) $R^1$, $R^2$, and $R^3$ are a C2 to C4 hydrocarbon when $R^1=R^2=R^3$, (b) $R^1$ and $R^2$ are a hydrocarbon group when $R^3$ is H, or (c) $R^1$ is a hydrocarbon group when $R^2$ and $R^3$ are H;
    introducing a reaction gas into the reactor at the same time or at an alternate time as the introduction of the cobalt-containing compound; and
    depositing at least part of the cobalt-containing compound onto the substrate to form the cobalt-containing film.

14. The method of claim 13, wherein the cobalt-containing compound is selected from the group consisting of $Et_3SiCo(CO)_4$, $nPr_3SiCo(CO)_4$, $iPr_3SiCo(CO)_4$, $nBu_3SiCo(CO)_4$, $sec-Bu_3SiCo(CO)_4$, $iBu_3SiCo(CO)_4$, $tBu_3SiCo(CO)_4$, $EtMeHSiCo(CO)_4$, $nPrMeHSiCo(CO)_4$, $iPrMeHSiCo(CO)_4$, $PhMeHSiCo(C_O)_4$, $Me_2HSiCo(CO)_4$, $Me_2iPrSiCo(CO)_4$, $Me_2nPrSiCo(CO)_4$, $Me_2nBuSiCo(CO)_4$, $Me_2(sec-Bu)SiCo(CO)_4$, $Me_2tBuSiCo(CO)_4$, $Me_2iBuSiCo(CO)_4$, $Me_2PhSiCo(CO)_4$, $Me_2HSiCo(CO)_4$, $Et_2HSiCo(CO)_4$, $Et_2MeSiCo(CO)_4$, $nPr_2HSiCo(CO)_4$, $iPr_2HSiCo(CO)_4$, $nBu_2HSiCo(CO)_4$, $sec-Bu_2HSiCo(CO)_4$, $iBu_2HSiCo(CO)_4$, $tBu_2HSiCo(CO)_4$, $Ph_2HSiCo(CO)_4$, $MeH_2SiCo(CO)_4$, $EtH_2SiCo(CO)_4$, $nPrH_2SiCo(CO)_4$, $iPrH_2SiCo(CO)_4$, $nBuH_2SiCo(CO)_4$, $sec-BuH_2SiCo(CO)_4$, $iBuH_2SiCo(CO)_4$, $tBuH_2SiCo(CO)_4$, and $PhH_2SiCo(CO)_4$.

15. The method of claim 14, wherein the cobalt containing compound is selected from the group consisting of $Et_2HSiCo(CO)_4$, $Et_3SiCo(CO)_4$, and $iPr_3SiCo(CO)_4$.

16. The method of claim 15, wherein the cobalt containing compound is $Et_3SiCo(CO)_4$.

17. The method of claim 13, wherein the reaction gas is a reducing agent selected from the group consisting of $N_2$, $H_2$, $NH_3$, $SiH_4$, $Si_2H_6$, $Si_3H_8$, $(Me)_2SiH_2$, $(C_2H_5)_2SiH_2$, $(CH_3)_3SiH$, $(C_2H_5)_3SiH$, $[N(C_2H_5)_2]_2SiH_2$, $N(CH_3)_3$, $N(C_2H_5)_3$, $(SiMe_3)_2NH$, $(CH_3)HNNH_2$, $(CH_3)_2NNH_2$, phenyl hydrazine, $B_2H_6$, $(SiH_3)_3N$, radical species of these reducing agents, and mixtures of these reducing agents.

18. The method of claim 17, wherein the reaction gas is $H_2$ and $NH_3$.

* * * * *